(12) United States Patent
Matsukawa et al.

(10) Patent No.: US 8,911,356 B2
(45) Date of Patent: Dec. 16, 2014

(54) ENDOSCOPE

(71) Applicant: Olympus Medical Systems Corp., Tokyo (JP)

(72) Inventors: Shiho Matsukawa, Hachioji (JP); Kazuhiko Hino, Hachioji (JP); Takafumi Kubo, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/096,232

(22) Filed: Dec. 4, 2013

(65) Prior Publication Data
US 2014/0094656 A1    Apr. 3, 2014

Related U.S. Application Data

(63) Continuation of application No. PCT/JP2012/073480, filed on Sep. 13, 2012.

(30) Foreign Application Priority Data

Jan. 31, 2012 (JP) ................................. 2012-018784

(51) Int. Cl.
  *A61B 1/04* (2006.01)
  *G02B 23/24* (2006.01)
  *A61B 1/00* (2006.01)
(52) U.S. Cl.
  CPC .............. *A61B 1/04* (2013.01); *G02B 23/2476* (2013.01); *A61B 1/00018* (2013.01); *A61B 1/0011* (2013.01); *A61B 1/00114* (2013.01); *A61B 1/00124* (2013.01); *A61B 1/00066* (2013.01)
  USPC ........................... 600/110; 600/130; 600/131

(58) Field of Classification Search
  CPC ...... H02G 11/02; B65D 85/04; B65H 75/362; B65H 7/364; A61B 1/00018
  USPC ............ 600/110, 131, 130; 174/135; 242/388
  See application file for complete search history.

(56) References Cited

U.S. PATENT DOCUMENTS

| 4,979,614 | A | * | 12/1990 | Ruhaut ......................... 206/702 |
| 5,810,714 | A | * | 9/1998 | Takamura et al. ............ 600/134 |
| 6,796,939 | B1 | * | 9/2004 | Hirata et al. .................. 600/179 |
| 2012/0006706 | A1 | * | 1/2012 | Coulson et al. ............... 206/388 |

FOREIGN PATENT DOCUMENTS

| JP | 08-211307 A | 8/1996 |
| JP | 09-098944 A | 4/1997 |
| JP | 2001-305435 A | 10/2001 |
| JP | 2002-250824 A | 9/2002 |
| JP | 2004-055877 A | 2/2004 |

OTHER PUBLICATIONS

International Search Report dated Oct. 16, 2012 issued in PCT/JP2012/073480.

* cited by examiner

*Primary Examiner* — Anhtuan T Nguyen
*Assistant Examiner* — Rynae Boler
(74) *Attorney, Agent, or Firm* — Scully, Scott, Murphy & Presser, P.C.

(57) ABSTRACT

An insertion portion, an operation portion, a signal cable, a plate-shaped member, an electric board, and a fixing member are included. The fixing member is formed into a U-shape in which a bottom surface, a top surface, a side surface and a fitting port are formed, and has a stopper for a surplus portion that is fitted in an inside formed, a distance between the bottom surface and the top surface is set to be slightly larger than a diameter in the surplus portion, and the surplus portion is configured not to be disposed in layers in a height direction of the side surface when the surplus portion is housed between the bottom surface and the top surface of the fixing member.

4 Claims, 12 Drawing Sheets

ENDOSCOPE

CROSS REFERENCE TO RELATED APPLICATION

This application is a continuation application of PCT/JP2012/073480 filed on Sep. 13, 2012 and claims benefit of Japanese Application No. 2012-018784 filed in Japan on Jan. 31, 2012, the entire contents of which are incorporated herein by this reference.

BACKGROUND OF THE INVENTION

1. Field of the Invention

The present invention relates to an endoscope including an insertion portion that is inserted into a subject, and an operation portion that is connected to a rear end in an insertion direction of the insertion portion.

2. Description of the Related Art

In recent years, endoscopes that are inserted into subjects have been widely used in medical fields and industrial fields. An endoscope enables observation of an inside of a subject by an elongated insertion portion being inserted into the subject.

Further, in a distal end portion provided at a distal end side in the insertion direction of the insertion portion of an endoscope (hereinafter, simply called a distal end side), a solid image pickup device such as a CCD and a CMOS (hereinafter, simply called an image pickup device) that picks up an image of the inside of a subject is provided.

Here, the image of a subject that is picked up by the image pickup device is displayed on a monitor or the like of an external apparatus by a connector that is located at an extension end of a universal cord that is extended from the operation portion connected to a rear end in the insertion direction of the insertion portion of the endoscope (hereinafter, simply called a rear end) being connected to the external apparatus.

Accordingly, in the insertion portion, the operation portion, the universal cord and the connector, a signal cable that transmits a video signal from the image pickup device is extended and inserted from the image pickup device to the connector.

Further, Japanese Patent Application Laid-Open Publication No. 8-211307 discloses the configuration that enhances repairability of a signal cable by providing a surplus portion in the signal cable that is located in the connector.

Furthermore, Japanese Patent Application Laid-Open Publication No. 8-211307 discloses the configuration that prevents the signal cable from being damaged by a tensile force that is applied to the signal cable with flexing of the insertion portion and bending of the bending portion provided at the insertion portion, by making the signal cable movable in the connector.

Further, the configuration is also well known, which prevents degradation of a video signal by dividing an intermediate position of a signal cable in such a manner that an electric board that amplifies a video signal is provided in the operation portion, the extension end of the first signal cable that is extended from the image pickup device and transmits a video signal is electrically connected to the electric board, and the video signal that is amplified by the electric board is transmitted to the connector by using the second signal cable that is extended from the electric board to the connector.

Further, in the configuration as above, similarly to Japanese Patent Application Laid-Open Publication No. 8-211307, the first signal cable needs to have a surplus portion in the operation portion so that repairability of the first signal cable is enhanced, and the first signal cable becomes movable in the operation portion.

Here, if the surplus portion of the signal cable becomes long, the radiation noise irradiated from the signal cable becomes large. For this reason, the configuration is also known, which dissipates the radiation noise of the signal cable to a plate-shaped member by disposing the surplus portion of the signal cable in close proximity to the plate-shaped member that is provided in the operation portion, fixes the components in the operation portion, and is configured by a metal.

More specifically, the configuration is also known, which fixes the surplus portion of the signal cable to the plate-shaped member by covering the surplus portion with use of a fixing member that has an opening toward the plate-shaped member and has a section in a U-shape facing down, for example, so that the surplus portion becomes movable.

SUMMARY OF THE INVENTION

An endoscope according to one aspect of the present invention includes an insertion portion that is inserted into a subject, an operation portion that is connected to a rear end in an insertion direction of the insertion portion, a signal cable that is extended to an inside of the operation portion from an image pickup device that is provided in an inside of a distal end side in the insertion direction of the insertion portion, and picks up an image of an inside of the subject, a plate-shaped member that is fixed to the inside of the operation portion and is configured by a metal, an electric board that is fixed to the plate-shaped member, and to which an extension end of the signal cable is electrically connected, and a fixing member that has a fixing portion to the plate-shaped member formed in a part thereof, and causes the signal cable to approach the plate-shaped member and be fixed thereto so that in a state in which a surplus portion that is located in the inside of the operation portion in the signal cable, has a plurality of U-shaped folded portions and is deformed into a loop shape is inserted through an inside by penetrating through openings at a front and at a rear in the insertion direction, the surplus portion becomes movable forward and backward in the insertion direction, wherein the fixing member is formed into a U-shape in which a bottom surface that abuts on the plate-shaped member and has the fixing portion, a top surface that faces the bottom surface and presses the surplus portion to the bottom surface side, a side surface that connects the bottom surface and the top surface, and a fitting port for fitting the surplus portion of the signal cable into the inside, which is opened at a position facing the side surface are formed, a stopper for the surplus portion that is fitted in the inside is formed on the bottom surface near the fitting port, and a distance between the bottom surface and the top surface is set to be slightly larger than a diameter in the surplus portion of the signal cable, and the surplus portion is configured not to be disposed in layers in a height direction of the side surface when the surplus portion is housed between the bottom surface and the top surface of the fixing member.

DETAILED DESCRIPTION OF THE PREFERRED EMBODIMENT

Hereinafter, an embodiment of the present invention will be described with reference to the drawings.

Figure 1:
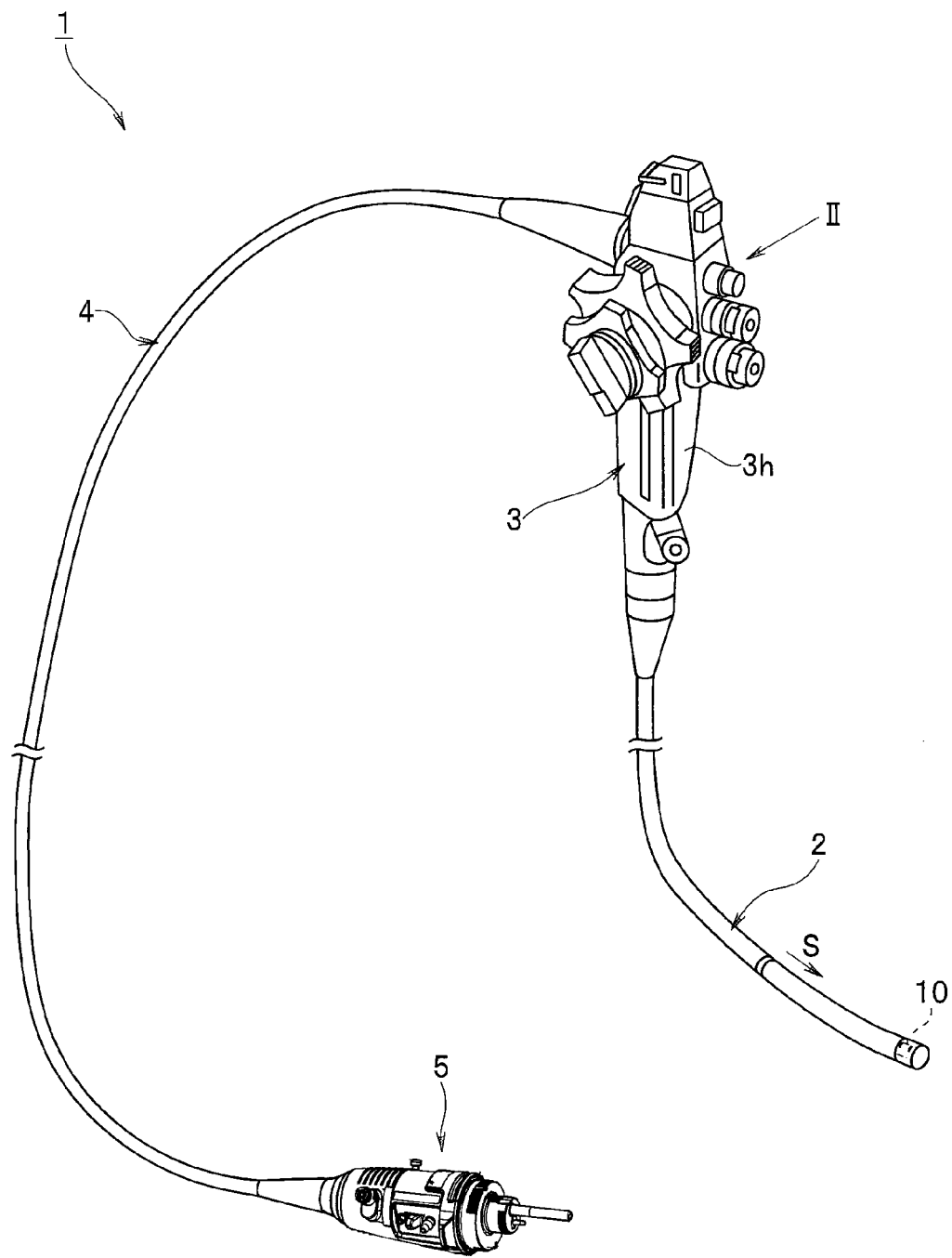
FIG. 1 is a perspective view showing an endoscope of the present embodiment.
Figure 2:
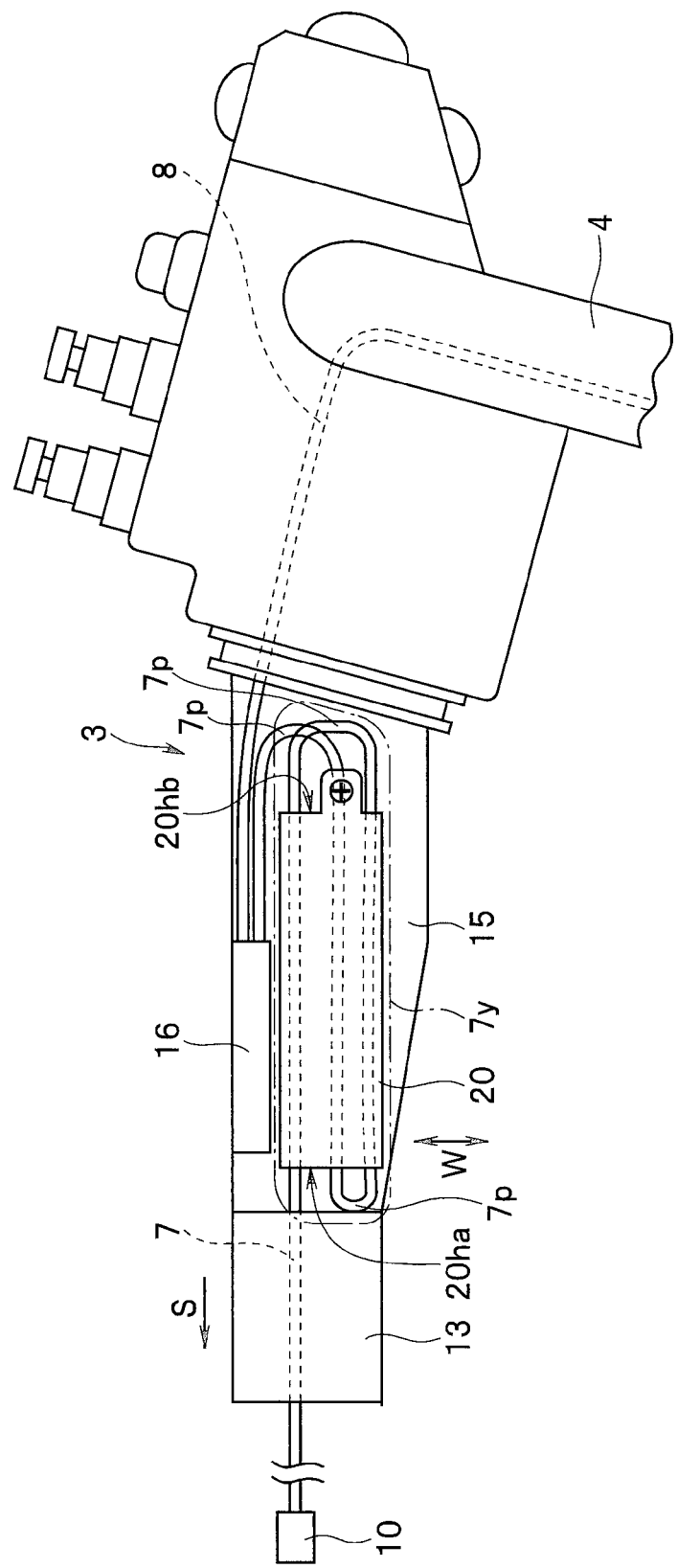
FIG. 2 is a plan view of an operation portion of the endoscope of FIG. 1 seen from the II direction in FIG. 1, in a state in which sheathing of a grasping portion is detached.
Figure 3:
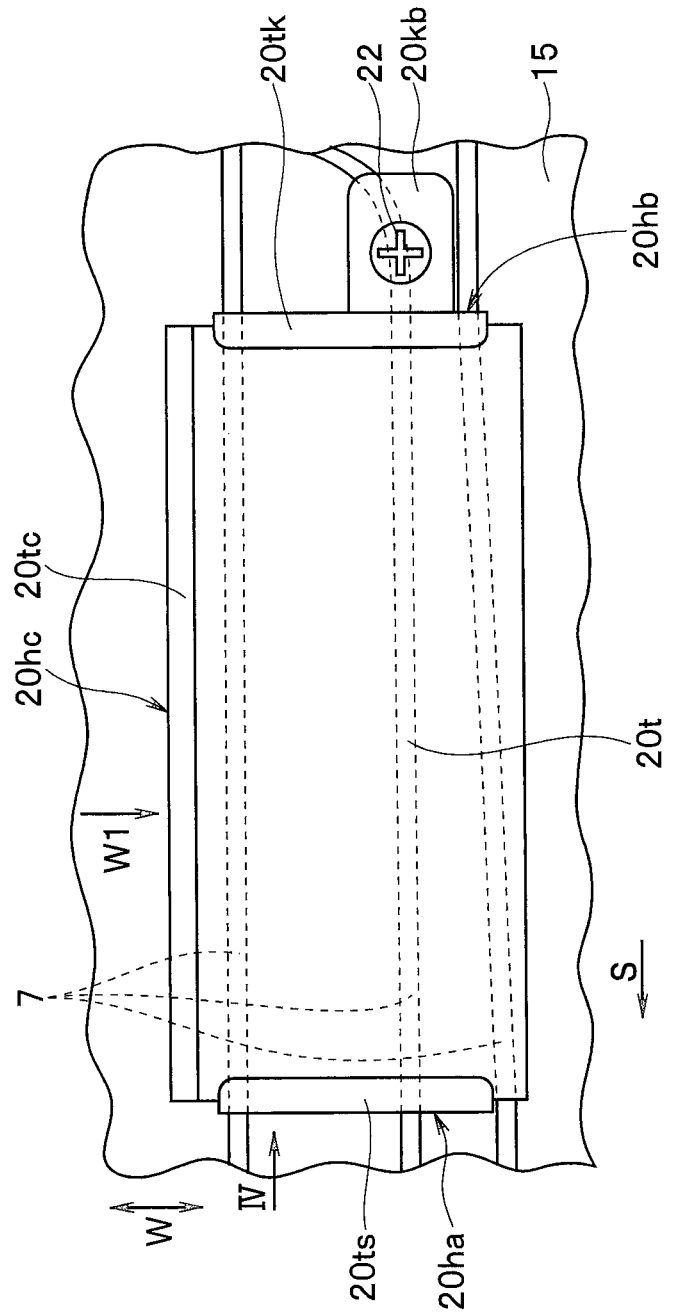
FIG. 3 is a plan view showing a fixing member of FIG. 2 with a part of a plate-shaped member and a part of a surplus portion under enlargement.

FIG. 1 is a perspective view showing an endoscope of the present embodiment. FIG. 2 is a plan view of an operation portion of the endoscope of FIG. 1 seen from the II direction in FIG. 1, in a state in which sheathing of a grasping portion is detached. FIG. 3 is a plan view showing a fixing member of FIG. 2 with a part of a plate-shaped member and a part of a surplus portion under enlargement.

Figure 4:
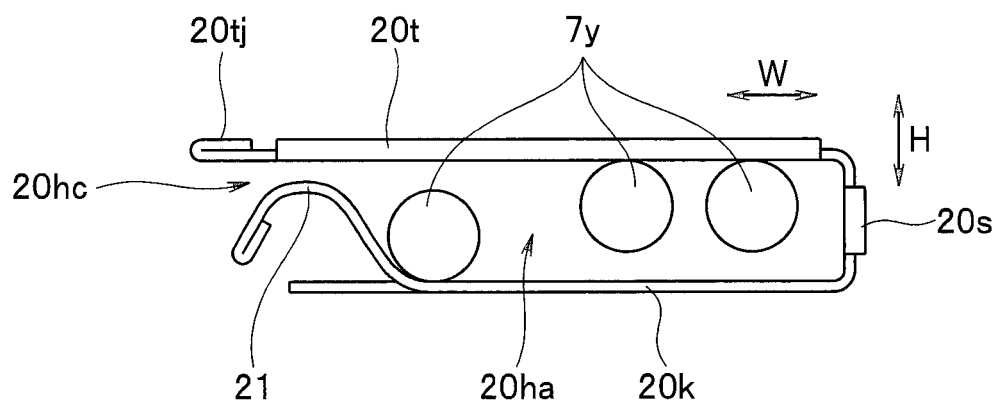
FIG. 4 is a side view of the fixing member of FIG. 3 seen from the direction of IV in FIG. 3 with the surplus portion of a signal cable.
Figure 5:
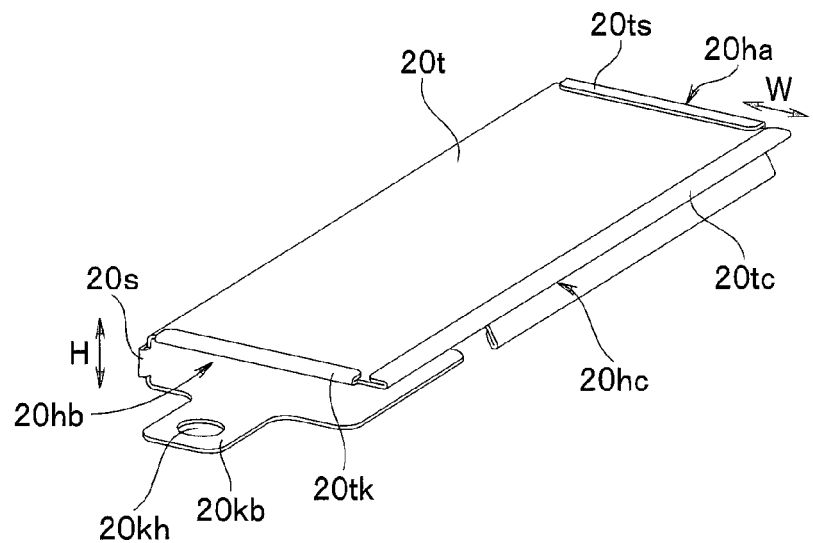
FIG. 5 is a perspective view of the fixing member of FIG. 3.
Figure 6:
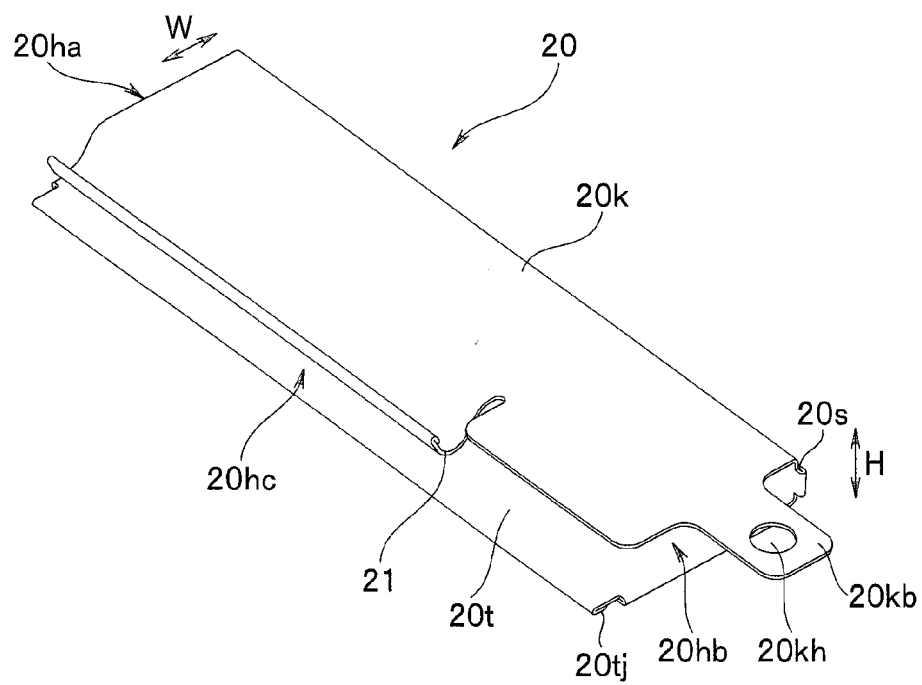
FIG. 6 is a perspective view of the fixing member of FIG. 5 seen from a bottom surface side.

Further, FIG. 4 is a side view of the fixing member of FIG. 3 seen from the direction of IV in FIG. 3 with the surplus portion of a signal cable. FIG. 5 is a perspective view of the fixing member of FIG. 3. FIG. 6 is a perspective view of the fixing member of FIG. 5 seen from a bottom surface side.

As shown in FIG. 1, an endoscope 1 has a main part configured by including an insertion portion 2 that is inserted into a subject, an operation portion 3 that is connected to a rear end of the insertion portion 2, a universal cord 4 that is extended from the operation portion 3, and a connector 5 that is provided at an extension end of the universal cord 4.

The operation portion 3 has a grasping portion 3h that is grasped by an operator, and is provided with a cylindrical member 13 to which a rear end of the insertion portion 2 is connected, in a distal end in an insertion direction S (hereinafter, simply called a distal end), as shown in FIG. 2.

Further, a plate-shaped member 15 that is fixed to the cylindrical member 13 and is configured by a metal is fixed to an inside of the operation portion 3. The plate-shaped member 15 is the member to which various components that are provided in the operation portion 3 are fixed.

Note that the connector 5 is connectable to an external apparatus, for example, a video processor or a light source apparatus that are known and are not illustrated, whereby the endoscope 1 is connectable to the external apparatus.

Further, in a distal end side of the insertion portion 2, an image pickup device 10 that picks up an image of an inside of a subject is provided, and from the image pickup device 10, a signal cable 7 that transmits a video signal of an image picked up by the image pickup device 10 is extended into the operation portion 3, as shown in FIG. 2.

A connector not illustrated is provided at an extension end of the signal cable 7, and the connector is electrically connected to a rear end of an electric board 16 that is fixed to the plate-shaped member 15.

The electric board 16 amplifies a video signal that is transmitted by the signal cable 7. Further, from the rear end of the electric board 16, another signal cable 8 that transmits the video signal that is amplified by the electric board 16 to the connector 5, and is different from the signal cable 7 is extended to the connector 5 via the universal cord 4. Namely, the signal cable 7 is electrically connected to the signal cable 8 via the electric board 16.

Further, as shown in FIG. 2, a surplus portion $7y$ of the signal cable 7 is located in the operation portion 3. Note that in the operation portion 3, the surplus portion $7y$ is provided at the signal cable 7, whereby repairability of the signal cable 7 is enhanced, and the surplus portion $7y$ becomes movable in the operation portion 3. Thereby, even if a tensile force in the insertion direction S is applied to the signal cable 7 with a distal end being connected to the image pickup device 10 and a rear end being connected to the electric board 16, with flexing of the insertion portion 2 and bending of a bending portion not illustrated that is provided at a distal end side of the insertion portion 2, the signal cable 7 can be prevented from being broken.

The surplus portion $7y$ has a plurality of, for example, three folded portions $7p$ and is deformed into a loop shape, more specifically is deformed into a loop shape to have one folded portion $7p$ at a front side in the insertion direction S and have the two folded portions $7p$ at a rear side in the insertion direction S, and the surplus portion $7y$ is caused to approach the plate-shaped member 15 and be fixed to the plate-shaped member 15 by the fixing member 20 so that the surplus portion $7y$ becomes movable forward and rearward only in the insertion direction S, in a state in which the surplus portion $7y$ penetrates through an opening $20ha$ at a distal end of the fixing member 20 and an opening $20hb$ at a rear end and is inserted through an inside of the fixing member 20 as shown in FIG. 2 and FIG. 4.

Note that it is for the purpose of dissipating a radiation noise of the surplus portion $7y$ to the plate-shaped member 15 that is configured by a metal that the surplus portion $7y$ of the signal cable 7 is caused to approach and be fixed to the plate-shaped member 15.

Further, the folded portion $7p$ is a site where the signal cable 7 folded to an opposite side by 180° in the insertion direction S. Furthermore, the number of folded portions $7p$ is not limited to three, but may be two, or four or more. Namely, the surplus portion $7y$ may be deformed into a loop shape by having two, or four or more folded portions $7p$.

Note that in FIG. 2, in the state in which the surplus portion $7y$ is fixed with use of the fixing member 20, a plurality of folded portions $7p$ are located outside the fixing member 20, but may be located in the fixing member 20.

Further, a plurality of folded portions 7p freely enter and exit an inside of the fixing member 20 with forward and backward movement in the insertion direction S of the surplus portion 7y, via the openings 20ha and 20hb.

As shown in FIG. 3 to FIG. 6, the fixing member 20 is formed into a shape having the opening 20ha at the distal end, the opening 20hb at the rear end, and a fitting port 20hc by being folded into a U-shape so that a bottom surface 20k, a top surface 20t, and a side surface 20s that connects the bottom surface 20k and the top surface 20t are integrated, to be elongated along the insertion direction S and have a predetermined width in a direction W (hereinafter, called an orthogonal direction) orthogonal to the insertion direction S.

Note that a distance between the bottom surface 20k and the top surface 20t, namely, a raised height H of the side surface 20s is formed to be a height slightly larger than a diameter of the surplus portion 7y that is fitted into the fixing member 20, as shown in FIG. 4. Namely, in the fixing member 20, the surplus portion 7y is not disposed in layers in a height direction of the side surface 20s.

The bottom surface 20k is a site that abuts on the plate-shaped member 15 when the fixing member 20 is fixed to the plate-shaped member 15, and is formed to have a predetermined width in the orthogonal direction W and to be elongated along the insertion direction S.

Further, as shown in FIG. 3, FIG. 5 and FIG. 6, at a rear end of the bottom surface 20k, a fixing portion 20kb that fixes the fixing member 20 to the plate-shaped member 15 is formed. In the fixing portion 20kb, a through-hole 20kh is formed. A screw 22 that is fitted in the through-hole 20kh is screwed into a screw hole not illustrated that is formed in the plate-shaped member 15, whereby the fixing member 20 is fixed to the plate-shaped member 15. Namely, the fixing member 20 is fixed to the plate-shaped member 15 only by one point of the fixing portion 20kb at the rear end.

This is because in the operation portion 3, a plurality of disposed matters are disposed with high density, and therefore, if a plurality of fixing portions 20kb are provided in the fixing member 20, a fixing work of the fixing member 20 to the plate-shaped member 15 becomes difficult. Therefore, if this is ignored, the fixing member 20 may be fixed to the plate-shaped member 15 with use of a plurality of fixing portions 20kb.

Further, as shown in FIG. 4 to FIG. 6, a stopper 21 that prevents the surplus portion 7y that is inserted through the inside of the fixing member 20 from protruding from the fitting port 20hc in the orthogonal direction W is formed along the insertion direction S, in a position near the fitting port 20hc in the bottom surface 20k. Note that the stopper 21 may be formed in a position near the fitting port 20hc in the top surface 20t.

The stopper 21 is configured by a leaf spring having a convex shape at a top surface 20t side. Note that by the stopper portion 21, and the side surface 20s, the bottom surface 20k and the top surface 20t, the surplus portion 7y is made movable only forward and rearward in the insertion direction S via the openings 20ha and 20hb.

The top surface 20t is located to face the bottom surface 20k, and is formed continuously to the bottom surface 20k via the side surface 20s, and is formed to have a predetermined width in the orthogonal direction W and to be elongated along the insertion direction S, similarly to the bottom surface 20k.

Note that in the operation portion 3, other members such as an air/water feeding tube and a light guide not illustrated are disposed on an upper surface at an opposite side from the bottom surface 20k, of the top surface 20t, and the top surface 20t also has a function of pressing the surplus portion 7y that is inserted through the inside of the fixing member 20 to a bottom surface 20k side, by being pressed to the bottom surface 20k side by the other members. Namely, the top surface 20t restrains the surplus portion 7y from protruding in the raised direction H of the side surface 20s from an interior of the fixing member 20.

Note that as shown in FIG. 4, since the top surface 20t does not press the surplus portion 7y to the bottom surface 20k without a clearance, namely, presses the surplus portion 7y to the bottom surface 20k with a gap, and therefore, the surplus portion 7y is movable forward and rearward in the insertion direction S in the fixing member 20.

Further, on the upper surface of the top surface 20t, the other members are disposed as described above, and therefore, at end portions at a distal end and a rear end of the top surface 20t, and at a fitting port 20hc side, folded portions 20ts, 20tk and 20tc at which the end portions are folded back by 180° are respectively formed as shown in FIG. 3 and FIG. 5 so that the other members that contact the top surface 20t are not damaged by edge portions of the top surface 20t.

The fitting port 20hc is opened along the insertion direction S in a position facing the side surface 20s, and is an opening for sliding and fitting the surplus portion 7y that is deformed into a loop shape by having a plurality of folded portions 7p into the fixing member 20 from a W1 direction in the orthogonal direction W as shown in FIG. 3, namely, from an electric board 16 side.

Next, a fixing method of the surplus portion 7y to the plate-shaped member 15 will be described.

First, a worker electrically connects the connector provided at the extension end of the signal cable 7 to the rear end of the electric board 16.

Thereafter, the worker deforms the surplus portion 7y of the signal cable 7 that is located in the operation portion 3 into a loop shape to have, for example, the three folded portions 7p, slides and fits the surplus portion 7y after deformation into the fixing member 20 to thereby make the cable 7 and the fixing member 20 one unit, and fits the unit to between the other members and the plate-shaped member 15 in the operation portion 3 from the orthogonal direction W.

Next, the worker causes the bottom surface 20k of the fixing member 20 to abut on the plate-shaped member 15, in the position adjacent to the electric board 16 in the orthogonal direction W.

On the above occasion, even if the other members such as the air/water feeding tube and the light guide are already disposed in the operation portion 3, only the bottom surface 20k or the side surface 20s abuts on the other members, in fitting of the fixing member 20 into the operation portion 3, namely, only surface portions abut on the other members, and therefore, the other members are not damaged, with fitting of the fixing member 20.

Further, in the state after fitting, the signal cable 7 in the surplus portion 7y penetrates through the opening 20ha at the distal end of the fixing member 20 and the opening 20h at the rear end. Further, a plurality of folded portions 7p of the surplus portion 7y are located outside the fixing member 20.

Furthermore, after fitting, the surplus portion 7y does not protrude from the fitting port 20hc, by the stopper 21 that is formed at the bottom surface 20k, and in addition, is made movable only forward and backward in the insertion direction S via the openings 20ha and 20hb by the stopper 21, and the side surface 20s, the bottom surface 20k and the top surface 20t.

Finally, via the through-hole 20kh of the fixing portion 20kb provided at the bottom surface 20k of the fixing member 20, the fixing portion 20kb is fixed to the plate-shaped member 15 by the screw 22, and thereby, the bottom surface 20k is fixed to the plate-shaped member 15 with only one point. Namely, in the state in which the surplus portion 7y has approached the plate-shaped member 15, the surplus portion 7y is fixed to the plate-shaped member 15 via the fixing member 20.

Note that electrical connection of the connector that is provided at the extension end of the signal cable 7 to the electric board 16, which has been performed at the beginning of assembly may be performed after the fixing member 20 is fixed to the plate-shaped member 15.

Further, unlike the assembly procedure described above, the fixing member 20 may be firstly fitted into the operation portion 3, the cable 7 may be slid and fitted into the fixing member 20, and the fixing member 20 may be fixed with two screws.

As above, in the present embodiment, it is shown that in the operation portion 3, the surplus portion 7y of the signal cable 7 is fitted into the fixing member 20 from the fitting port 20hc of the U-shaped fixing member 20 in the state in which the surplus portion 7y of the signal cable 7 has a plurality of folded portions 7p and is deformed into a loop shape, and the fixing portion 20kb of the bottom surface 20k of the fixing member 20 is fixed to the plate-shaped member 15 with the screw 22.

It is shown that thereby, the surplus portion 7y of the signal cable 7 is caused to approach the plate-shaped member 15 and be fixed to the plate-shaped member 15 in the state in which the surplus portion 7y is restrained from protruding from the fitting port 20hc by the stopper 21 at the bottom surface 20k of the fixing member 20, and is movable only forward and backward in the insertion direction S via the openings 20ha and 20hb by the stopper 21, the side surface 20s, the bottom surface 20k and the top surface 20t.

According to the above, even if the other members such as the air/water feeding tube and the light guide are already disposed in the operation portion 3, the edge portion of the opening end of the fixing member 20 does not contact the other members in fitting of the fixing member 20 into the operation portion 3, as in the conventional endoscope, but only the bottom surface 20k or the side surface 20s abuts on the other members, and therefore, does not damage the other members, with fitting of the fixing member 20.

Further, when the surplus portion 7y is fitted into the fixing member 20, work can be performed with a sufficient space, and by making the fixing member 20 and the surplus portion 7y one unit, assembling work to the operation portion 3 is facilitated.

Furthermore, the fixing member 20 can be fitted into the operation portion 3 by being slid from the orthogonal direction W, and therefore, even in the operation portion 3 in which the disposed matters are disposed with high density, the fixing member 20 can be disposed in a clearance that is made between the plate-shaped member 15 and the other members without damaging the other disposed matters.

Furthermore, when the fixing member 20 is fitted into the operation portion 3 in advance and is fixed with the screws after the cable 7 is slid and fitted into the fixing member 20, the surplus portion 7y can be fitted into the fixing member 20 by being slid and moved from a narrow gap between the fixing member 20 and the electric board 16 via the fitting port 20hc, at the time of the surplus portion 7y being fitted into the fixing member 20. Thereby, even if the disposed matters are disposed in the operation portion 3 with high density, the surplus portion 7y does not contact the other members in the operation portion 3, and the surplus portion 7y can be easily fitted into the fixing member 20 by the small number of working steps with favorable workability.

Further, it is not necessary to fix the fixing member 20 that is put on the surplus portion 7y to the plate-shaped member 15 while pressing the surplus portion 7y to the plate-shaped member 15, as in the conventional endoscope, and therefore, fixing of the surplus portion 7y to the plate-shaped member 15 can be easily performed with favorable workability with use of the fixing member 20.

Furthermore, the surplus portion 7y in the fixing member 20 is pressed to the bottom surface 20k side by the top surface 20t of the fixing member 20, and therefore, the surplus portion 7y can be fixed to the plate-shaped member 15 as close as possible to the plate-shaped member 15. Accordingly, not only the radiation noise of the surplus portion 7y can be efficiently dissipated to the plate-shaped member 15, but also the loop shape of the surplus portion 7y can be stably held even in the operation portion 3 in which the disposed matters are disposed with high density.

Further, not only the surplus portion 7y in the fixing member 20 does not protrude from the fitting port 20hc by the stopper 21 at the bottom surface 20k, but also the surplus portion 7y is freely movable only forward and backward in the insertion direction S via the openings 20ha and 20hb by the stopper 21, and the side surface 20s, the bottom surface 20k and the top surface 20t, namely, the moving direction of the surplus portion 7y is defined. Thereby, it does not occur that in the operation portion 3 in which the disposed matters are disposed with high density, the surplus portion 7y moves in an unintended direction and the other members in the operation portion 3 are damaged by the surplus portion 7y.

Further, the top surface 20t of the fixing member 20 does not press the surplus portion 7y to the bottom surface 20k without a clearance as shown in FIG. 4, and therefore, the surplus portion 7y can freely move.

From the above, the endoscope 1 can be provided, which has the configuration that can fix the surplus portion 7y to the plate-shaped member 15 by using the fixing member 20 while defining the moving direction of the surplus portion 7y of the signal cable 7 without inhibiting movement of the surplus portion 7y, and with ease without damaging the other members, in the operation portion 3.

The aforementioned fixing member can take the configuration as follows.

The surplus portion 7y of the signal cable is wound on a cylindrical member such as a bobbin, for example, and this is fixed to the plate-shaped member 15 in a rotatable state. The bobbin is brought into a rotatable state, whereby even if a tensile force is applied to the signal cable 7, the signal cable 7 can be prevented from being damaged. Further, in the configuration like this, a ferrite core is combined with the aforementioned bobbin, or the bobbin itself is given a ferrite core function, whereby the radiation noise of the signal cable 7 can be reduced.

APPENDIXES

As described in detail above, according to the embodiment of the present invention, the configuration as follows can be obtained. Namely, (1) An endoscope having an endoscope connector that is connected to an external apparatus,
wherein the endoscope connector includes
a first case,
a fitting portion that is attachable to and detachable from one end side in an extending direction of the first case, has an electric contact point formed on an outer circumferential face, and is fittable in the external apparatus, a second case that is attachable to and detachable from the other end side in the extending direction of the first case, a first electric board that is provided on a surface at the first case side in the fitting portion, and is electrically connected to the electric contact point, a second electric board that is provided along the extending direction in the first case and the second case, has an image pickup cable that is extended from an image pickup device connected to the other end in the extending direction, and has one end side half portion in the extending direction fitted into the first case from the other end in the extending direction of the first case in a state in which the second case is removed from the first case, and a signal cable that has a first extending site and a second extending site that are along the extending direction and are located to face a side surface along the extending direction of the second electric board in at least the first case, and a folded portion that is folded back by 180° at a distal end side in the extending direction to the second extending site from the first extending site, in which one end extending from the first extending site in the first case is electrically connected to the first electric board, and the other end provided in the second extending site is electrically connected to one end in the extending direction of the second electric board.

(2) The endoscope according to appendix 1, wherein the folded portion is located in the second case, and when the second case is removed from the first case, the folded portion is exposed to an outside.

(3) The endoscope according to appendix 1 or 2, further including:

a metal shield member that covers the second electric board; and a holding member that has a clip portion that keeps and holds a shape along the extending direction of the second extending site in the signal cable, and is fixed to the metal shield member with the clip portion.

(4) The endoscope according to any one of appendixes 1 to 3, wherein the first extending site in the signal cable is formed to be more rigid than the second extending site and the folded portion.

(5) The endoscope according to any one of appendixes 1 to 4, wherein in one end in the extending direction of the first case, a sheet metal member is fixed to between the first electric board and the second electric board in the extending direction, and the sheet metal member is provided with a cutout that keeps a shape along the extending direction of the first extending site in the signal cable and performs positioning of the first extending site, and a stopper that prevents dislocation of the first extending site from the cutout.

Incidentally, in recent years, endoscopes have been widely used in the medical field and the industrial field. An endoscope enables observation of an inside of a subject by an elongated insertion portion being inserted into a subject.

Further, in a distal end portion provided at a distal end side in the insertion direction of the insertion portion of an endoscope, a solid image pickup device such as a CCD and a CMOS (hereinafter, simply called an image pickup device) that picks up an image of the inside of a subject is provided.

Here, the image of a subject that is picked up by the image pickup device is displayed on a monitor or the like of an external apparatus by an endoscope connector that is located at an extension end of a universal cord that is extended from the operation portion of an endoscope being connected to the external apparatus such as a video processor or a light source apparatus.

Accordingly, in the insertion portion, the operation portion, the universal cord and the endoscope connector, an image pickup cable that transmits a video signal from the image pickup device is extended and inserted from the image pickup device to the endoscope connector.

Further, Japanese Patent Application Laid-Open Publication No. 8-211307 discloses the configuration that holds a surplus portion of an image pickup cable that is located in an endoscope connector and has a rear end electrically connected to a contact pin that is an electric contact point by winding the surplus portion on an outer periphery of a shield cylinder.

However, the configuration disclosed in Japanese Patent Application Laid-Open Publication No. 8-211307 is a configuration in which the image pickup cable is electrically connected to the contact pin in the endoscope connector, and therefore, has the problem that connection of the image pickup cable to the contact pin is difficult.

Further, a configuration is also known, in which a surplus portion is not provided in the image pickup cable, but the first electric board that is electrically connected to an electric contact point, and a second electric board to which the image pickup cable is electrically connected are provided in an endoscope connector, and the two electric boards are electrically connected with a signal cable having a surplus portion.

However, in the configuration, the signal cable has to be housed in a narrow space that is invisible from a worker in the endoscope connector, and therefore, the configuration has not only the possibility that the worker breaks the signal cable if the worker forcefully houses the signal cable into the narrow space, or forcefully pushes the signal cable into an invisible position, but also the problem that the worker cannot confirm whether the signal cable is housed to be in the shape as designed.

An object of the present appendix is made in the light of the above described problem, and is to provide an endoscope that includes a configuration that can easily connect an image pickup cable to a second electric board, and can house a signal cable in an endoscope connector by stabilizing a shape of the signal cable that electrically connects the second electric board and the first electric board.

Hereinafter, a specific configuration will be described with use of FIG. 7 to FIG. 12.

Figure 7:
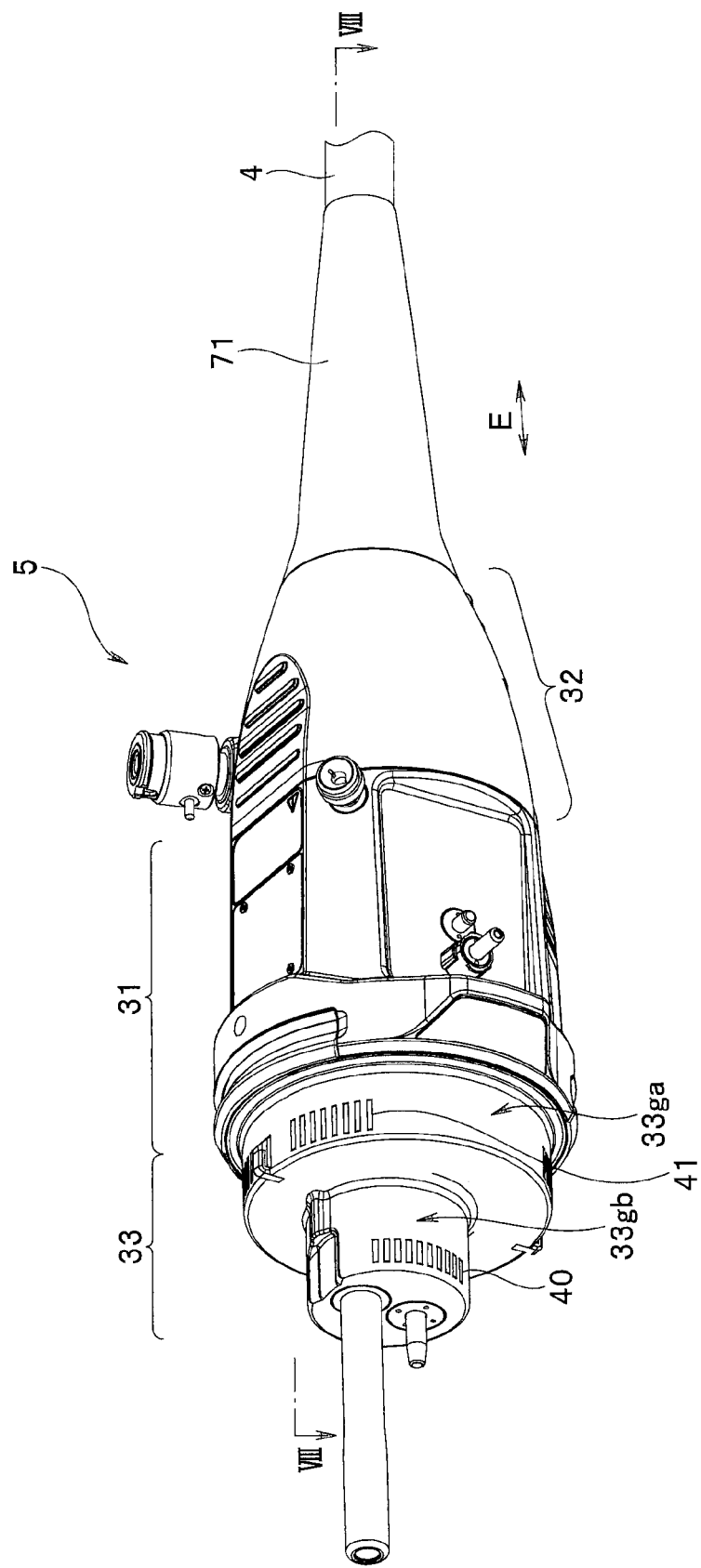
FIG. 7 is a partial perspective view showing an endoscope connector that is connected to an external apparatus, in an endoscope of an appendix.
Figure 8:
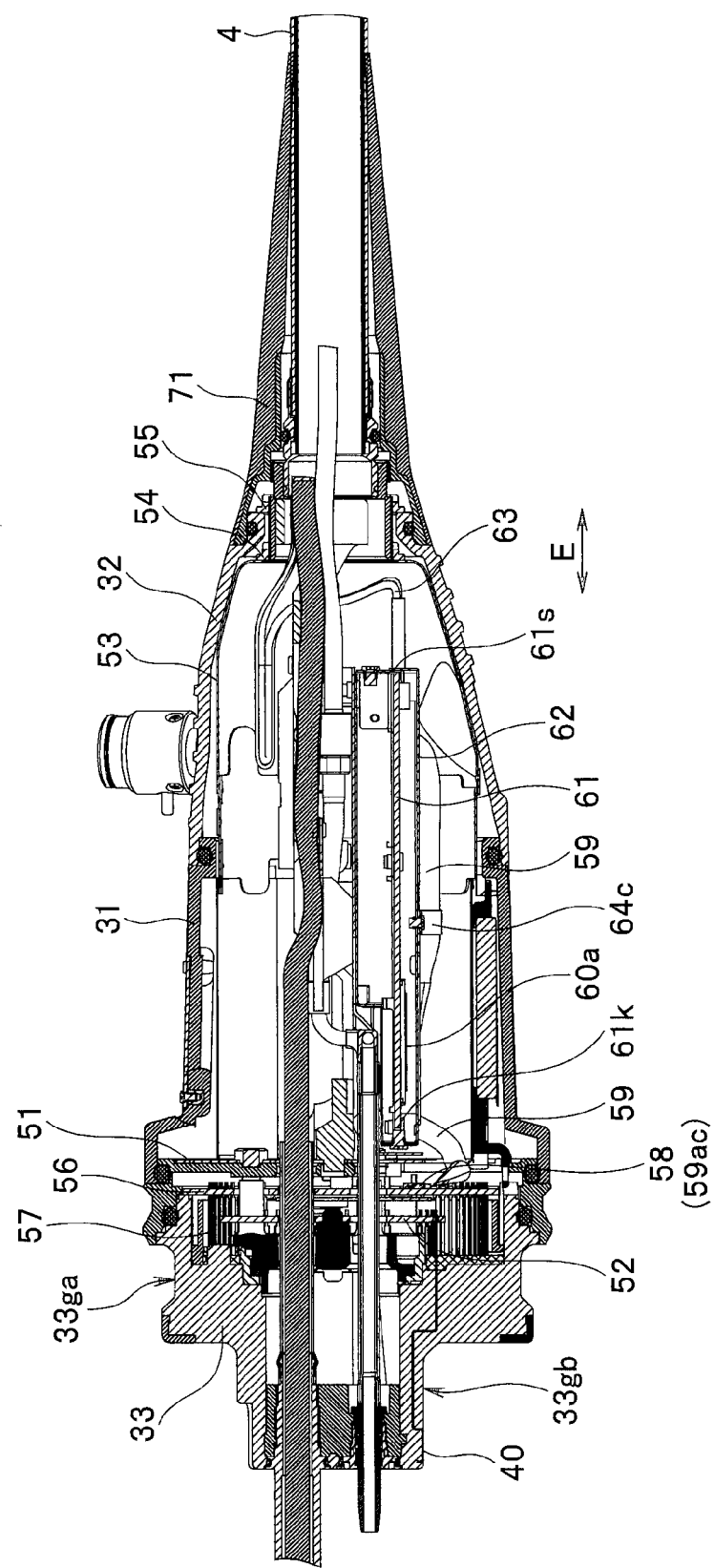
FIG. 8 is a sectional view of the endoscope connector along the VIII-VIII line in FIG. 7.
Figure 9:
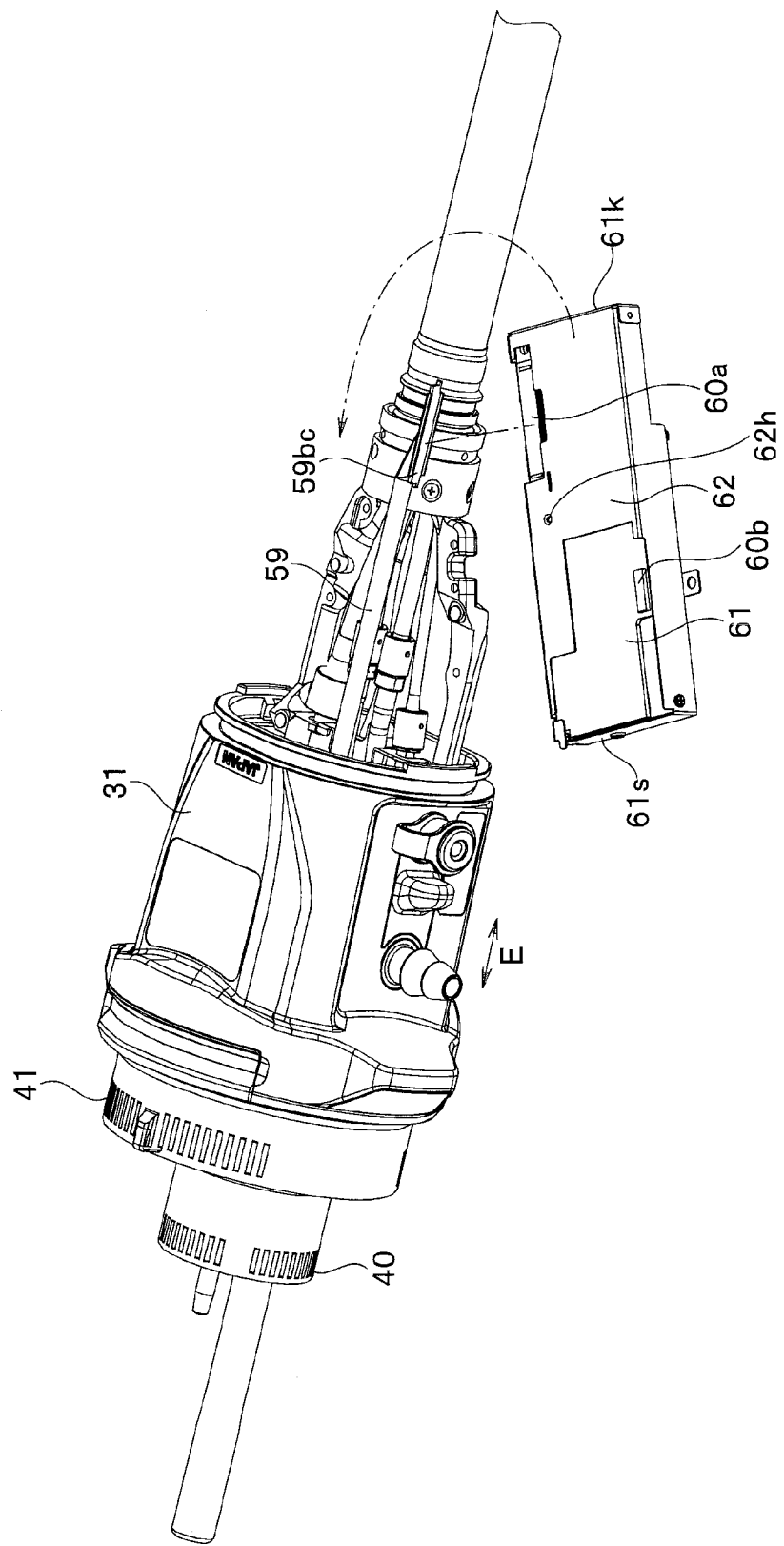
FIG. 9 is a perspective view showing a state in which a second case is removed from the endoscope connector of FIG. 7, and a second electric board is detached from the signal cable.

FIG. 7 is a partial perspective view showing an endoscope connector that is connected to an external apparatus, in the endoscope of the present appendix. FIG. 8 is a sectional view of the endoscope connector along the VIII-VIII line in FIG. 7. FIG. 9 is a perspective view showing a state in which a second case is removed from the endoscope connector of FIG. 7, and a second electric board is detached from the signal cable.

Figure 10:
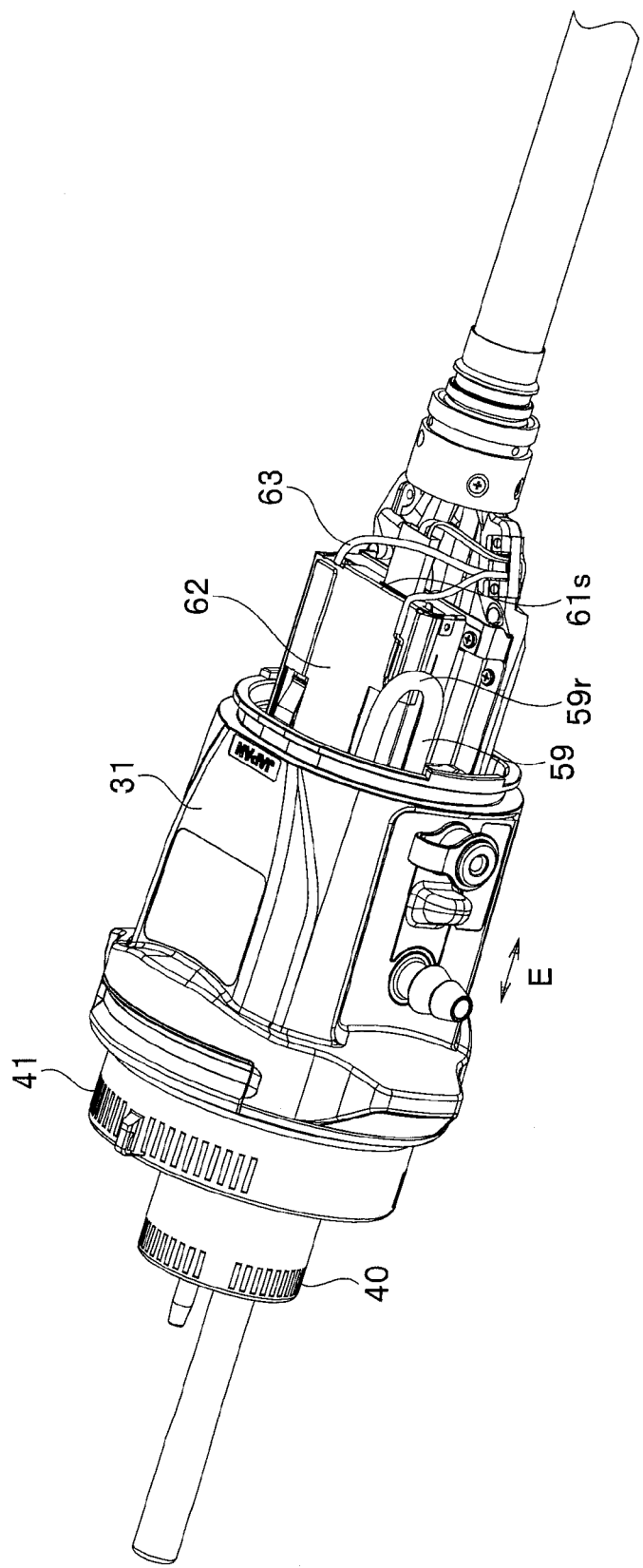
FIG. 10 is a perspective view showing a state in which the signal cable is electrically connected to the second electric board of FIG. 9, and the second electric board is housed in the first case.
Figure 11:
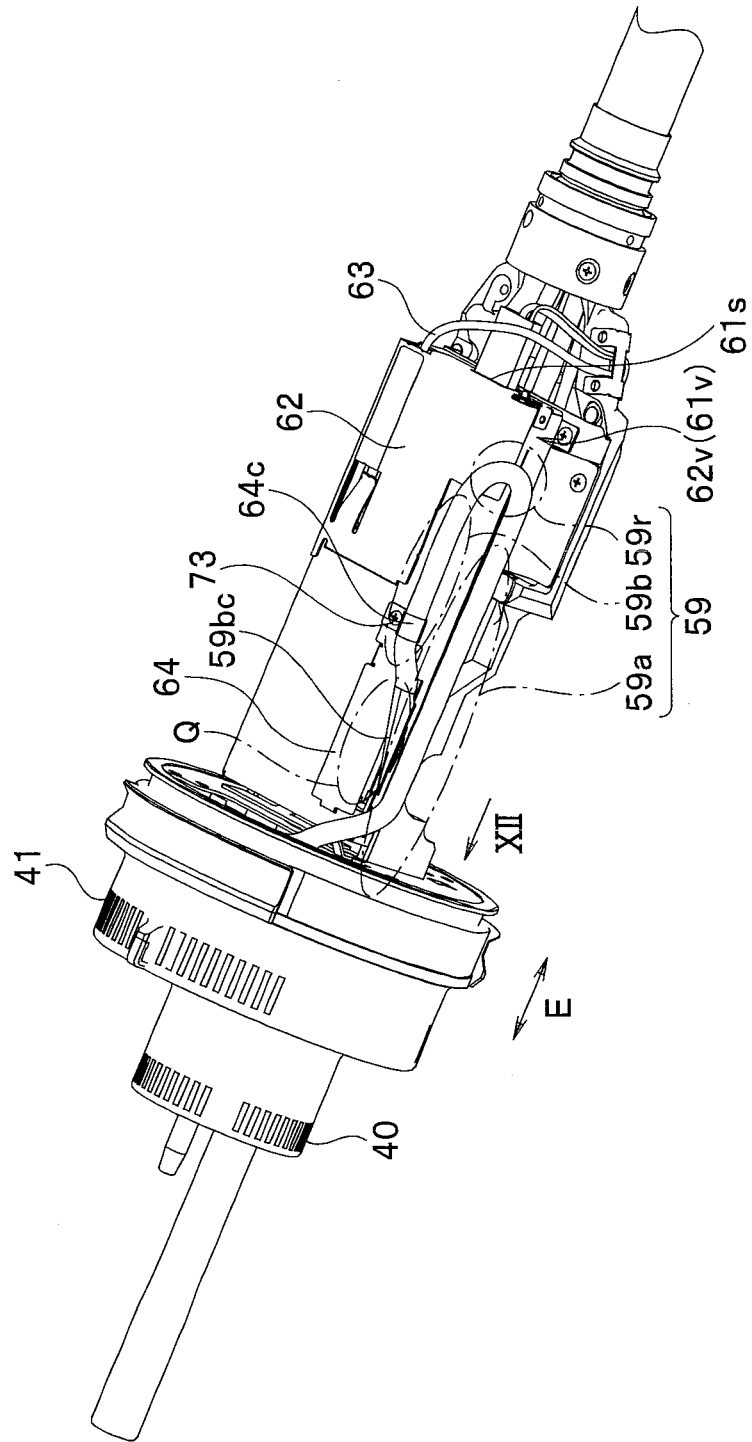
FIG. 11 is a perspective view showing a state in which the first case is removed from the endoscope connector of FIG. 10.
Figure 12:
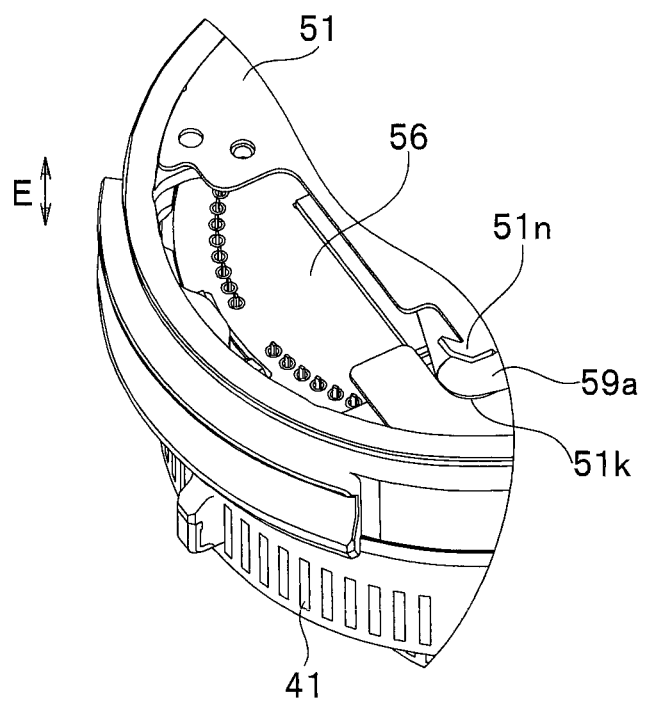
FIG. 12 is a partial perspective view of a fitting portion of FIG. 11 seen from the XII direction in FIG. 11.

Further, FIG. 10 is a perspective view showing a state in which the signal cable is electrically connected to the second electric board of FIG. 9, and the second electric board is housed in the first case. FIG. 11 is a perspective view showing a state in which the first case is removed from the endoscope connector of FIG. 10. FIG. 12 is a partial perspective view of a fitting portion of FIG. 11 seen from the XII direction in FIG. 11.

Note that hereinafter, in FIG. 7 to FIG. 12, the endoscope connector 5 will be described, in which the other end side in an extending direction E that is at a universal cord 4 side will be called a distal end side in the extending direction E (hereinafter, simply called a distal end side), and one end side in the extending direction E at a side that is an opposite side from the universal cord 4 and is a side to be connected to an external apparatus will be called a rear end side in the extending direction E (hereinafter, simply called a rear end side). Accordingly, one end in the extending direction E will be called a rear end, and the other end in the extending direction E will be called a distal end.

As shown in FIG. 7, the endoscope connector 5 that is connected to an external apparatus not illustrated such as a video processor and a light source apparatus has a first case 31, a fitting portion 33 that is attachable to and detachable from a rear end side of the first case 31, and a second case 32 that is attachable to and detachable from a distal end side of the first case 31.

Note that a bend preventer 71 is connected to a distal end of the second case 32, and the universal cord 4 is extended to a front in the extending direction E (hereinafter, simply called a front) via the bend preventer 71.

As shown in FIG. 7 and FIG. 8, the fitting portion 33 has an outer circumferential face 33*ga* with a large diameter, and an outer circumferential face 33 *gb* that is located at a rear end side from the outer circumferential face 33*ga* and has a smaller diameter than that of the outer circumferential face 33*ga*. On the outer circumferential face 33*ga*, a plurality of electric contact points 41 are exposed, and on the outer circumferential face 33 *gb*, a plurality of electric contact points 40 are exposed.

Note that the electric contact points 40 and 41 are used when the endoscope performs transmission and reception of electric signals to and from the external apparatus by being electrically connected to electric contact points of the external apparatus when the fitting portion 33 is connected to the external apparatus.

Further, as shown in FIG. 8, a first electric board 56 is fixed to a distal end face that is a surface at a first case 31 side of the fitting portion 33. A plurality of contact pins 57 with distal end sides penetrating through the first electric board 56 along the extending direction E are fixed to the first electric board 56 by soldering or the like, and rear ends in the extending direction E of the contact pins 57 (hereinafter, simply called rear ends) are exposed to an outer surface as the electric contact points 40 and 41 (the electric contact points 41 are not illustrated in FIG. 8).

Further, on a distal end face of the first electric board 56, an electric connector 58 to which one end 59*ac* of a signal cable 59 is electrically connectable is provided in a rear end in the first case 31.

Furthermore, as shown in FIG. 8, in the first case 31 and the second case 32, a second electric board 61 for video processing is provided along the extending direction E. Note that an outer periphery of the second electric board 61 is covered with a metal shield member 62 that electrically shields the second electric board 61, as shown in FIG. 8 to FIG. 11.

As shown in FIG. 8, the second case 32 is fixed to a distal end in the extending direction of the first case 31 (hereinafter, simply called a distal end) by a metal ring 55 that is provided at a distal end of the second case 32.

Further, in the second case 32, a shield case 53 that covers various components provided in a front half potion that is a half portion at the other end side in the endoscope connector 5, and is configured by a metal is provided, and the shield case 53 is fixed by a metal ring 54 in a distal end in the second case 32.

Accordingly, if the metal ring 55 is detached, the second case 32 is detached from the first case 31, and if the metal ring 54 is detached, the shield case 53 is detached from the first case 31.

Note that the first case 31 does not become detached from the endoscope connector 5. However, in FIG. 11, in order to make an inside of the first case 31 understandable, the endoscope connector 5 is shown with the first case 31 detached.

Further, in the second electric board 61 that is provided in the first case 31 and the second case 32, at a rear end 61*k* side of an upper surface of the second electric board 61, an electric connector 60*a* to which the other end 59*bc* of the signal cable 59 is electrically connectable is provided in a rear end in the first case 31.

Further, in the second electric board 61, at a distal end 61*s* side of the upper surface, an electric connector 60*b* to which a connector (not illustrated) at an extension end of an image pickup cable 63 that is extended from the image pickup device 10 (see FIG. 1) is electrically connected is provided.

Note that the reason why the electric connectors 60*a* and 60*b* are located separately at the distal end 61*s* and the rear end 61*k* in the extending direction E, on the upper surface of the second electric board 61, is that a large surface area of the board for use in circuit design is desired to be used, in circuit design of the second electric board 61, namely, a signal is desired to be inputted from the distal end 61*s* and outputted from the rear end 61*k*.

Note that the one end 59*ac* of the signal cable 59 is electrically connected to the first electric board 56, and the other end 59*bc* is electrically connected to the second electric board 61, whereby the first electric board 56 and the second electric board 61 are electrically connected via the signal cable 59.

As shown in FIG. 9 and FIG. 10, the second electric board 61 is located with a part thereof is fitted into the first case 31 from the distal end of the first case 31, in a state in which the second case 32 is removed from the first case 31.

More specifically, as shown in FIG. 9, in an outside of the first case 31, in a state in which the outer periphery of the second electric board 61 is covered with the metal shield member 62, and in a state in which the distal end 61*s* of the second electric board 61 directs to a rear in the extending direction E (hereinafter, simply called a rear), and the rear end 61*k* of the second electric board 61 directs to the front, the other end 59*bc* of the signal cable 59 is electrically connected to the electric connector 60*a* exposed from the metal shield member 62, after which, the second electric board 61 is rotated by 180° to an orientation in which the rear end 61*k* directs to the rear and the distal end 61*s* directs to the front, and thereafter, as shown in FIG. 10, a rear half portion that is a half portion at one end side in the extending direction E of the second electric board 61 is fitted from the distal end of the first case 31 to be located in the first case 31.

Note that after the second electric board 61 is fitted into the first case 31, a connector 63*c* of the image pickup cable 63 is electrically connected to the electric connector 60*b* at the front half portion that is located outside the first case 31, in front of the first case 31.

As above, since the electric connector 60*b* is located outside the first case 31, the connector 63*c* of the image pickup cable 63 is electrically connected thereto easily.

As shown in FIG. 11, the signal cable 59 that electrically connects the first electric board 56 and the second electric board 61 has a main part configured by having, in at least the first case 31, a first extending site 59*a* and a second extending site 59*b* that are along the extending direction E of the second electric board 61 and the metal shield member 62, and a folded portion 59*r* that is folded by 180° in the distal end to the second extending site 59*b* from the first extending site 59*a*. Note that the second extending site 59*b* is located forward of the first extending site 59*a*.

Namely, the signal cable 59 has a predetermined length, and is configured such that the first extending site 59a is extended to the front from the one end 59ac and is folded by the folded portion 59r that is located at the distal end of the first extending site 59a, the second extending site 59b is extended to the rear from the folded portion 59r, and the other end 59bc provided at an extension end of the second extending site 59b is electrically connected to the electric connector 60a of the second electric board 61.

Note that the reason why the signal cable 59 is formed to have a predetermined length by having the first extending site 59a, the second extending site 59b and the folded portion 59r is that as described above, in the second electric board 61, the other end 59bc of the signal cable 59 is electrically connected to the electric connector 60a in the state in which the rear end 61k directs to the front, after which, the second electric board 61 is rotated by 180°, and thereafter, the rear half portion is fitted into the first case 31, and therefore, if the signal cable 59 does not have the predetermined length, electrical connection of the other end 59bc to the electric connector 60a cannot be performed, outside the first case 31.

In other words, this is because after the deposition, the electric connector 60a is located in the rear end of the first case 31, and therefore, work of electrically connecting the other end 59bc to the electric connector 60a in the first case 31 is very difficult.

Further, as shown in FIG. 8 and FIG. 10, the folded portion 59r is located in the second case 32. Namely, when the second case 32 is removed from the first case 31, the folded portion 59r is located to be exposed outside the first case 31 in front of the first case 31.

As described above, after the other end 59bc of the signal cable 59 is electrically connected to the electric connector 60a, the second electric board 61 is rotated by 180°, and is fitted into the first case 31 from the rear end 61k side, whereby as shown in FIG. 10 and FIG. 11, the first extending site 59a and the second extending site 59b are almost located in the first case 31. Namely, the first extending site 59a and the second extending site 59b are housed in the position where they are invisible by the worker.

Accordingly, it is difficult for the worker to confirm whether the first extending site 59a and the second extending site 59b are located in the stable shapes along the extending direction E in the first case 31 as designed.

However, if the folded portion 59r is located outside the first case 31 as shown in FIG. 10, the worker can easily visually confirm whether the first extending site 59a and the second extending site 59b are located in the stable shapes along the extending direction E in the first case 31 as designed, according to the separation distance of the folded portion 59r in the extending direction from the distal end of the first case 31.

More specifically, if the worker visually recognizes that the folded portion 59r protrudes by the predetermined length to the front from the distal end of the first case 31, the worker can judge that it is normal. If the worker visually recognizes that the protruding distance of the folded portion 59r is small, or the folded portion 59r does not protrude, the worker can judge that the first extending site 59a and the second extending site 59b are located in the first case 31 by being twisted by fitting work of the second electric board 61 into the first case 31, namely, that it is not normal.

Note that as the configuration that stabilizes the housing state of the second extending site 59b in the first case 31, a configuration that uses a holding member 64 is also conceivable as shown in FIG. 11.

More specifically, as shown in FIG. 8, FIG. 9 and FIG. 11, the plate-shaped holding member 64 is fixed to an upper surface of the metal shield member 62 by a screw 73 being screwed into a screw hole 62h (see FIG. 9) provided on the upper surface. Note that the holding member 64 covers a connection portion of the other end 59bc of the signal cable 59 to the electric connector 60a.

Thereby, fixing of the holding member 64 to the upper surface of the metal shield member 62 is performed after the other end 59c of the signal cable 59 is electrically connected to the electric connector 60a of the second electric board 61 in the outside of the first case 31.

Further, as shown in FIG. 8 and FIG. 11, the holding member 64 has a clip portion 64c that keeps and holds the shape along the extending direction E of the second extending site 59b, in the first case 31.

The clip portion 64c covers an outer periphery near the other end 59bc, of the second extending site 59b, and is fixed to the screw hole 62h by the screw 73 with a part of the holding member 64.

According to the above, a space between an inner circumferential face of the distal end of the first case 31 and the second extending site 59b can be reliably ensured, and therefore, contact of the second extending site 59b to the inner circumferential face of the distal end of the first case 31 can be avoided.

Therefore, the second extending site 59b is not located by being twisted in the first case 31 by fitting work of the second electric board 61 into the first case 31, and therefore, the shape of the second extending site 59b in the first case 31 can be stabilized.

Namely, a traveling direction of the second extending site 59b is restrained by the clip portion 64c, whereby the second extending site 59b can be kept in the shape that is along the extending direction E, and therefore, breakage of the second extending site 59b can be prevented.

Further, the first extending site 59a is formed to be more rigid than the second extending site 59b and the folded portion 59r.

More specifically, the first extending site 59a is formed to be rigid and difficult to curve by having the outer periphery covered with a protection tape, by having a core metal put therein, by having rigidity of the resin made more rigid than that of the other sites, by being configured by a metal pipe, or the like. Note that the configuration of making the first extending site 59a rigid is not limited thereto.

This is for the purpose of preventing the first extending site 59a from being crushed, or buckled, when the other end 59bc of the signal cable 59 is electrically connected to the electric connector 60a of the rear end 61k of the second electric board 61 that is located in front of the first case 31, and thereafter, the second electric board 61 is rotated by 180° and is fitted into the first case 31 from the rear end 61k side, from the distal end of the first case 31.

Here, if the signal cable 59 is made rigid throughout the entire length, the second extending site 59b and the folded portion 59r are difficult to curve. Thereby, contrary to the first extending site 59a, the second extending site 59b and the folded portion 59r are preferably formed to be as soft as possible, because the second extending site 59b and the folded portion 59r are sites that move when the other end 59bc of the signal cable 59 is electrically connected to the electric connector 60a of the rear end 61k of the second electric board 61 that is located in front of the first case 31, and thereafter, the second electric board 61 is rotated by 180° and is fitted into the first case 31 from the rear end 61k side, from the distal end of the first case 31.

According to the above, when the second electric board 61 is housed into the first case 31, the shapes of the first extending site 59*a* and the second extending site 59*b* can be stabilized, and breakage of the signal cable 59 can be prevented.

Returning to FIG. 8, a plate-shaped member 51 is fixed to an inside of the rear end of the first case 31 along the diameter direction of the first case 31 in a position between the first electric board 56 and the second electric board 61 in the extending direction E.

As shown in FIG. 12, in the plate-shaped member 51, a cutout 51*k* that causes the first extending site 59*a* with the one end 59*ac* electrically connected to the electric connector 58 in the fitting portion 33 to advance into the first case 31 is formed to penetrate through the plate-shaped member 51 along the extending direction E, and a stopper 51*n* that prevents dislocation of the first extending site 59*a* from the cutout 51*k*, and is formed by folding a part of the plate-shaped member 51 is formed.

The cutout 51*k* keeps the shape along the extending direction E of the first extending site 59*a* in the signal cable 59, and performs positioning of the first extending site 59*a* in the extending direction E and the diameter direction.

According to the above configuration, when the other end 59*bc* of the signal cable 59 is electrically connected to the electric connector 60*a* of the rear end 61*k* of the second electric board 61 that is located in front of the first case 31, and thereafter the second electric board 61 is rotated by 180° and is fitted into the first case 31 from the rear end 61*k* side, from the distal end of the first case 31, the first extending site 59*a* is housed by being folded to a region Q above the holding member 64 shown in FIG. 11, and the first extending site 59*a* is likely to be broken, but owing to the cutout 51*k*, the first extending site 59*a* is not folded to the region Q, and can be stably kept in the shape along the extending direction E as shown in the solid line of FIG. 11.

From the above, owing to the first extending site 59*a* being formed to be rigid, the second extending site 59*b* and the folded portion 59*r* being formed to be soft, the clip portion 64*c* of the holding member 64, and the cutout 51*k* of the plate-shaped member 51, the first extending site 59*a* and the second extending site 59*b* can be disposed in the stable shapes by only the second electric board 61 being fitted, in the inside of the first case 31 which is invisible by the worker.

Further, since the folded portion 59*r* is exposed from the first case 31, the worker can easily visually recognize that the first extending site 59*a* and the second extending site 59*b* are disposed in the stable shapes in the first case 31.

Further, connection of the connector 63*c* of the image pickup cable 63 to the electric connector 60*b* of the second electric board 61 is performed in the state exposed from the distal end of the first connector 31, and therefore, the connector 63*c* can be easily connected to the electric connector 60*b*.

From the above, the endoscope can be provided, which includes the configuration in which the image pickup cable 63 can be easily connected to the second electric board 61, and the signal cable 59 that electrically connects the second electric board 61 and the first electric board 56 can be housed in the endoscope connector 5 with the shape of the signal cable 59 being stabilized.

APPENDIX

As described in detail above, according to the present embodiment, a configuration as follows can be obtained. Namely, (6) An endoscope, including:
a flexible printed board; and
a convex portion that is integrally provided at the flexible printed board for at least a part of the flexible printed board, has a convex shape by a reinforcing plate and is a non-wired region,
wherein the convex portion abuts on another electric board different from the flexible printed board, whereby the flexible printed board is positioned to the other electric board, and an insulation property is ensured.

Incidentally, in a case in which a flexible printed circuit (hereinafter, called an FPC) and another electric board are disposed in close proximity to each other, the FPC easily moves after the FPC is disposed because it is difficult to fix a disposed position thereof by a screw or the like. Therefore, in order to ensure electric insulation of at least some of circuits of the FPC to at least some of circuits of the other electric board, it is necessary to wind an insulative tape on an outer periphery of the FPC, cover the outer periphery of the FPC with an insulative heat-shrinkable tube, or provide a spacer such as a member with a conductive circuit different from at least some of the circuits of the FPC and some of the circuits of the other electric board, and an insulative member in between the FPC and the other electric board.

However, in the above configuration, not only an assembly omission of the spacer is likely to occur to between the FPC and the other electric board, but also an insulative tape has to be wound, or the heat-shrinkable tube has to be put on, and therefore, the problem of the operability being unfavorable arises.

An object of the present appendix is made in the light of the above described problem, and is to provide an endoscope including a configuration capable of easily disposing a flexible board and another electric board in close proximity to each other with an insulation property ensured therebetween with a simple configuration.

Figure 13:
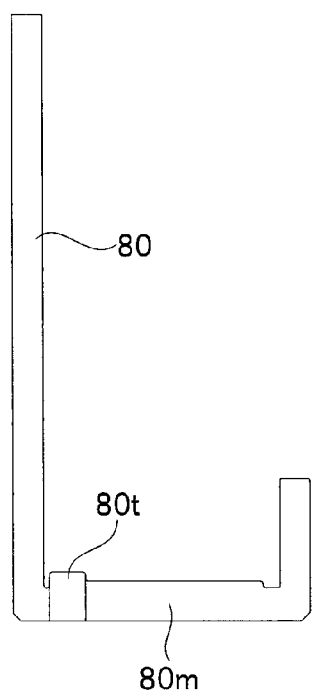
FIG. 13 is a plan view showing an FPC with which an outer periphery of a contact pin of FIG. 8 is covered by developing the FPC.
Figure 14:
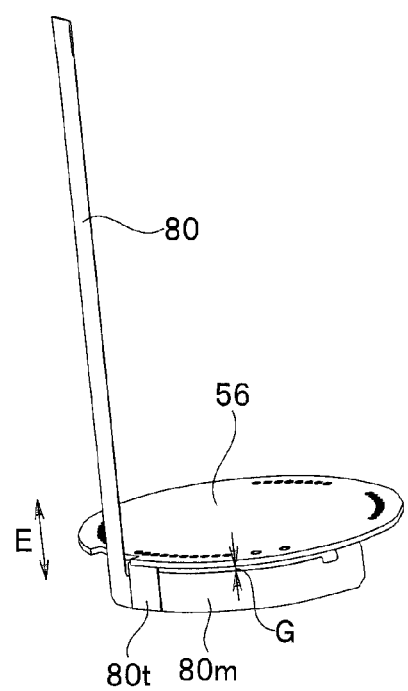
FIG. 14 is a perspective view showing a state in which a convex portion of the FPC of FIG. 13 is caused to abut on a first electric board of FIG. 8.

Hereinafter, a specific configuration will be described with use of FIG. 8, FIG. 13 and FIG. 14. FIG. 13 is a plan view showing an FPC with which the outer periphery of the contact pin of FIG. 8 is covered by developing the FPC. FIG. 14 is a perspective view showing a state in which a convex portion of the FPC of FIG. 13 is caused to abut on the first electric board.

As shown in FIG. 13, an FPC 80 that is formed into a hook shape in a state developed into a planar shape is located with the outer periphery of the contact pin 57 shown in FIG. 8 covered with a transverse portion 80*m* in a circular arc shape as shown in FIG. 14, and as shown in FIG. 8, some of circuits are electrically connected to the electric contact points 40 and 41 (the electric contact point 41 is not illustrated in FIG. 8) via the electric board 52, and the contact pin 57 soldered to the electric board 52.

When the outer periphery of the contact pin 57 is covered with the transverse portion 80*m* of the FPC 80, the other first electric board 56 different from the FPC 80 is provided along a direction orthogonal to the extending direction E, in front of the transverse portion 80*m*. Further, in the first electric board 56, some of circuits are also electrically connected to the electric contact points 40 and 41 (the electric contact point 41 is not illustrated in FIG. 8) via the contact pin 57 soldered to the electric board 52, and are electrically connected to the electric board 52 (see FIG. 8) that is located in the rear from the first electric board 56 via a connector not illustrated.

Here, in order to insulate some of the circuits described above in the FPC 80 from the other circuits different from some of the circuits in the first electric board 56 adjacent along the extending direction E, a convex portion 80*t* that has a convex shape by a reinforcing plate and is a non-wired region is integrally formed by a same outer sheath resin as the transverse portion 80*m* in at least a part of the transverse portion 80*m* of the FPC 80, as shown in FIG. 13 and FIG. 14, and as shown in FIG. 14, the convex portion 80*t* abuts on the first electric board 56. Note that the convex portion 80*t* may be formed in the entire transverse portion 80*m*.

By abutment of the convex portion 80*t* onto the first electric board 56, a distance G is ensured between an entire circumference of the transverse portion 80*m* and the first electric board 56 in the extending direction E as shown in FIG. 14, and the transverse portion 80*m* is positioned to the first electric board 56 in the extending direction E.

According to the above, by abutment of the convex portion 80*t* onto the first electric board 56, movement of the transverse portion 80*m* in the extending direction E is restrained, namely, the transverse portion 80*m* is positioned to the first electric board 56 in the extending direction E, and the distance G can be ensured between the first electric board 56 and the transverse portion 80*m*. Thereby, some of the circuits of the transverse portion 80*m* can be prevented from contacting the other circuits of the first electric board 56 that are objects to be insulated with respect to some of the circuits in the transverse portion 80*m* of the FPC 80.

Note that the convex portion 80*t* is formed to be a non-wired region, and therefore, even if the convex portion 80*t* abuts on the first electric board 56, some of the circuits of the transverse portion 80*m* do not electrically continue to the other circuits that are objects to be insulated of the first electric board 56.

Accordingly, it becomes unnecessary to assemble a spacer to between the transverse portion 80*m* and the first electric board 56 as in the conventional endoscope, and therefore, occurrence of an assembly omission of a spacer can be prevented.

Further, the convex portion 80*t* is integrally formed in the transverse portion 80*m*, and therefore, if the outer periphery of the contact pin 57 is covered with the transverse portion 80*m*, some of the circuits of the transverse portion 80*m* and the other circuits that are the objects to be insulated of the first electric board 56 are insulated so that assemblability of the FPC 80 is not impaired.

From the above, the endoscope can be provided, which includes the configuration in which the FPC 80 and the other electric board 56 can be easily disposed in close proximity to each other with an insulation property ensured, with the simple configuration.

Note that as the other electric board different from the FPC 80, the electric board 56 is cited as an example, but the other board is not limited to a rigid board, and may be an FPC as a matter of course.

What is claimed is:

1. An endoscope comprising:
an insertion portion that is inserted into a subject;
an operation portion that is connected to a rear end in an insertion direction of the insertion portion;
a signal cable that is extended to an inside of the operation portion from an image pickup device that is provided in an inside of a distal end side in the insertion direction of the insertion portion, and picks up an image of an inside of the subject;
a plate-shaped member that is fixed to the inside of the operation portion and is configured by a metal;
an electric board that is fixed to the plate-shaped member, and to which an extension end of the signal cable is electrically connected;
a surplus portion that is a surplus of the signal cable and is located in the operation portion, the surplus portion being deformed into a loop shape having a plurality of U-shaped folded portions;
a fixing member fixed to the plate-shaped member and having openings at a front and at a rear in the insertion direction, the fixing member causing the surplus portion to approach the plate-shaped member such that the surplus portion is movable forward and backward in the insertion direction in a state where the surplus portion has penetrated the openings and is inserted into an inside of the fixing member; and
a fixing portion formed at a part of the fixing member, the fixing portion fixing the fixing member to the plate-shaped member,
wherein the fixing member is formed into a U-shape in which a bottom surface that abuts on the plate-shaped member and has the fixing portion,
a top surface that faces the bottom surface and presses the surplus portion to the bottom surface side,
a side surface that connects the bottom surface and the top surface, and
a fitting port for fitting the surplus portion of the signal cable into the inside, which is opened at a position facing the side surface
are formed,
wherein the fixing member includes a stopper for the surplus portion that is fitted in the inside of the fixing member, the stopper being formed on the bottom surface near the fitting port, and
wherein the side surface has a raised height between the bottom surface and the top surface, the raised height being set to be slightly larger than a diameter in the surplus portion of the signal cable, and
wherein the surplus portion is configured not to be disposed in layers in a height direction of the side surface along the raised height when the surplus portion is housed between the bottom surface and the top surface of the fixing member.

2. The endoscope according to claim 1,
wherein the stopper is configured by a leaf spring having a convex shape on the top surface side.

3. The endoscope according to claim 1,
wherein the fixing portion is provided at a rear end in the insertion direction of the bottom surface, and
the fixing member is fixed to the plate-shaped member by one point of the fixing portion in the bottom surface.

4. The endoscope according to claim 1, further comprising:
a universal cord that extends from the operation portion, and has a connector that is connected to an external apparatus formed at an extension end,
wherein another signal cable that is extended from the electric board in the operation portion to the connector via the universal cord, and transmits a signal that is from the image pickup device and is transmitted to the electric board via the signal cable, and is different from the signal cable is included.

* * * * *